US010426856B2

(12) United States Patent
Kawasaki et al.

(10) Patent No.: US 10,426,856 B2
(45) Date of Patent: Oct. 1, 2019

(54) DECONTAMINATION SYSTEM

(71) Applicant: Airex Co., Ltd., Nagoya-shi, Aichi (JP)

(72) Inventors: Koji Kawasaki, Nagoya (JP); Daisuke Kakuda, Nagoya (JP); Jun Masudome, Nagoya (JP)

(73) Assignee: AIREX CO., LTD., Nagoya-Shi, Aichi (JP)

( * ) Notice: Subject to any disclaimer, the term of this patent is extended or adjusted under 35 U.S.C. 154(b) by 297 days.

(21) Appl. No.: 15/300,729

(22) PCT Filed: Apr. 30, 2014

(86) PCT No.: PCT/JP2014/061968
§ 371 (c)(1),
(2) Date: Sep. 29, 2016

(87) PCT Pub. No.: WO2015/166554
PCT Pub. Date: Nov. 5, 2015

(65) Prior Publication Data
US 2017/0014540 A1    Jan. 19, 2017

(51) Int. Cl.
*A61L 2/22* (2006.01)
*F24F 3/16* (2006.01)
(Continued)

(52) U.S. Cl.
CPC .............. *A61L 2/22* (2013.01); *A61L 2/208* (2013.01); *F24F 3/16* (2013.01); *A61L 2202/25* (2013.01);
(Continued)

(58) Field of Classification Search
CPC .............. A61L 2/22; A61L 2/208; F24F 3/16
See application file for complete search history.

(56) References Cited

U.S. PATENT DOCUMENTS

2006/0027507 A1*  2/2006  van Leeuwen ......... B63B 13/00
                                                        210/760

FOREIGN PATENT DOCUMENTS

JP    2001-37862    2/2001
JP    2002-231709   8/2002
(Continued)

OTHER PUBLICATIONS

English translation of JP2001037862 (Year: 2001).*
PCT/JP2014/061968 International Search Report with English translation.

*Primary Examiner* — Regina M Yoo
(74) *Attorney, Agent, or Firm* — Gavin J. Milczarek-Desai; Quarles & Brady LLP (57) ABSTRACT

[Problem] Provided is a decontamination system which does not require large scale equipment such as large diameter ducts or anti-condensation heaters, while enabling, with respect to a plurality of rooms targeted to be decontaminated, pipelining of which distance is long for each room, the decontamination system being capable of supplying an accurate amount of decontamination gas for each room.
[Solving Means] Compressed air-generating means and decontamination solution-supplying means are included, mixed gas-liquid adjusters and gas generators are respectively provided in each room targeted to be decontaminated, and a conveyance distance of gas-liquid supplying pipes which communicate with the mixed gas-liquid adjusters and the gas generators is longer than a conveyance distance of decontamination solution supplying pipes which communicate with decontamination solution-supplying means and the mixed gas-liquid adjusters.

6 Claims, 3 Drawing Sheets

(51) Int. Cl.
*A61L 2/20* (2006.01)
*C12M 1/12* (2006.01)

(52) U.S. Cl.
CPC ...... *C12M 37/00* (2013.01); *F24F 2003/1675* (2013.01)

(56) References Cited

FOREIGN PATENT DOCUMENTS

| | | |
|---|---|---|
| JP | 2005-160903 | 6/2005 |
| JP | 2006-320392 | 11/2006 |
| JP | 2010-179943 | 8/2010 |
| JP | 2010-235209 | 10/2010 |

\* cited by examiner

DECONTAMINATION SYSTEM

TECHNICAL FIELD

The present invention relates to a decontamination system for carrying out decontamination by generating decontamination gas in a room such as a sterile room, a clean room, or a hospital room.

BACKGROUND ART

In manufacturing fields of manufacturing medical or pharmaceutical products or foods or in medical fields such as a surgical room, it is important to maintain a sterile state in the room. In particular, in decontamination of the sterile room that is a working room intended to manufacture medical or pharmaceutical products, there is a need to complete advanced decontamination validation which conforms to the GMP (Good Manufacturing Practice).

In recent years, for the purpose of decontamination of a working room such as a sterile room (hereinafter, referred to as a "room targeted to be decontaminated"), hydrogen peroxide gas is employed in place of formalin gas which is harmful for a human body. This hydrogen peroxide gas has a strong sterile effect and is inexpensive and easily available, and eventually, is effective as an environmentally acceptable decontamination gas to decompose into oxygen and water. However, the hydrogen peroxide gas has been conventionally available for use in decontamination of a small space such as an isolator or a glove box. On the other hand, there has been a problem that, in order to employ the hydrogen peroxide gas for decontamination, in a large space such as the room targeted to be decontaminated, a large amount of the hydrogen peroxide gas of a predetermined concentration must be stably supplied.

Therefore, in Patent Literature 1 given below, there is proposed a sterile liquefying apparatus as a decontamination gas generator in which concentration control of sterile gas (hydrogen peroxide gas) is easy, and moreover, a large amount of sterile gas (hydrogen peroxide gas) can be supplied. This sterile liquefying apparatus is intended to evaporate hydrogen peroxide water in air which has been heated to a high temperature by heating means to thereby generate hydrogen peroxide gas, and is provided with two temperature sensors at a downstream side of evaporating means. Due to a temperature difference between these temperature sensors, heating means is controlled, and the hydrogen peroxide gas concentration is stabilized.

CITATION LIST

Patent Literature

Patent Literature 1: Japanese Unexamined Patent Application Publication No. 2003-339829

SUMMARY OF INVENTION

Problem to be Solved by Invention

A large amount of hydrogen peroxide gas which has been generated by these decontamination gas generators is obtained by gasifying hydrogen peroxide water, and is established in a state of mixture gas between hydrogen peroxide and water vapor. This hydrogen peroxide gas has a low density, and is supplied to a room targeted to be decontaminated, via large diameter ducts. Therefore, in order to stably supply to the room targeted to be decontaminated the hydrogen peroxide gas that is adjusted to a predetermined concentration by the decontamination gas generator, there is a need to fully heat the duct by a heater. If the heating exerted by the heater is insufficient, the supplied hydrogen peroxide gas condenses in the duct, and the supply concentration and supply quantity relative to the room targeted to be decontaminated becomes insufficient. Also, there has been a problem that the hydrogen peroxide solution generated by condensation is heated, and the inside of the duct is corroded.

Thus, there has been a problem that construction of large diameter ducts, heater equipment to heat the ducts and other ducts made of an anti-corrosion material are required to supply a large amount of hydrogen peroxide gas from the decontamination gas generator to the room targeted to be decontaminated.

Further, in the fields for manufacturing medical or pharmaceutical products, the number of rooms targeted to be decontaminated is not limited to one, and there is a need to decontaminate a plurality of rooms targeted to be decontaminated, at the same time. In this case, it is not effective to provide the decontamination gas generator as in the Patent Literature 1 for each room targeted to be decontaminated and then carry out duct construction as to each decontamination gas generator. Therefore, ducts of which distance is long are arranged from a single decontamination gas generator to the plurality of rooms targeted to be decontaminated and then from the duct, a branch duct is arranged in each room targeted to be decontaminated, and decontamination is thereby carried out at the same time. In this case, condensation is prone to occur at the branch portion of the duct, and a distance from the decontamination gas generator to each room targeted to be decontaminated is different from another one; and therefore, there has been a problem that it is impossible to accurately keep track of what amount of hydrogen peroxide gas has been supplied.

On the other hand, as a method for decontaminating each room targeted to be decontaminated without using large diameter ducts, it is contemplated to supply hydrogen peroxide water of high density before gasified, to each room targeted to be decontaminated, by a supplying pipe of which diameter is small and then carry out gasification near or in each room targeted to be decontaminated. In this case, gasification near or in each room targeted to be decontaminated is made possible by precipitating the supplied hydrogen peroxide water in a small evaporator (such as a heating version).

In addition, in comparison with the large diameter ducts in gas supply, the supplying pipe of which diameter is small in solution supply is easy in construction, and even if a pipelining construction is made for each room targeted to be decontaminated, costs thereof are reduced. Further, there is no need to heat hydrogen peroxide water to be supplied and thus there is no need to heat the supplying pipe, and corrosion in the pipe is also mitigated. However, in this method, hydrogen peroxide water always remains in the supplying pipe of which diameter is small, and a large amount of dead solution is generated in a lot of long pipes which are arranged for each room targeted to be decontaminated. Thus, there has been a problem that it is impossible to accurately keep track of what amount of hydrogen peroxide water has been supplied to each room targeted to be decontaminated.

Accordingly, the present invention has been made in order to solve the problems described above, and it is an object of the present invention to provide a decontamination system which does not require large scale equipment such as large diameter ducts or anti-condensation heaters, while enabling, with respect to a plurality of rooms targeted to be decontaminated, pipelining of which distance is long for each room, the decontamination system being capable of supplying an accurate amount of decontamination gas for each room.

Means for Solving the Problems

In order to solve the problems described above, the Inventor, et al., reached completion of the present invention by utilizing a supplying pipe of which diameter is small, to thereby supply, via the supplying pipe to each room targeted to be decontaminated, a mixture mist obtained by mixing hydrogen peroxide water in compression air and then gasifying the mixture mist near or in each room targeted to be decontaminated, to thereby generate hydrogen peroxide gas.

That is, a decontamination system according to the present invention, according to claim 1, is directed to a decontamination system (100) for decontaminating, with respect to one or more rooms targeted to be decontaminated (R1 to R4), an inside of each room targeted to be decontaminated, by using decontamination gas, the decontamination system having compressed air-generating means (10) for generating compression air and decontamination solution-supplying means (20) for supplying decontamination solution which is a source of generation of decontamination gas, the decontamination system comprising:

mixed gas-liquid adjusters (31 to 35) to adjust, with respect to each room targeted to be decontaminated, decontamination mixed gas-liquid obtained by respectively mixing the compression air and the decontamination solution;

gas generators (41 to 45) to gasify the mixed gas-liquid to generate decontamination gas;

air supplying pipes (11 to 15) which communicate from the compressed air-generating means up to the mixed gas-liquid adjuster;

decontamination solution-supplying pipes (21 to 25) which communicate from the decontamination solution-supplying means up to the mixed gas-liquid adjuster; and mixed gas-liquid supplying pipes (61 to 65) which communicate from the mixed gas-liquid adjuster up to the gas generator, characterized in that the compressed air-generating means, the decontamination solution-supplying means, and the respective mixed gas-liquid adjusters are arranged at positions which are spaced from each room targeted to be decontaminated, and each of the gas generators is arranged near or in each of the corresponding rooms targeted to be decontaminated, and a conveyance distance of the mixed gas-liquid supplying pipe with respect to each room targeted to be decontaminated is longer than a conveyance distance of each of the decontamination solution supplying pipes.

Also, the present invention, according to claim 2, is directed to the decontamination system according to claim 1, characterized in that, of one or more rooms targeted to be decontaminated, as to at least one or all of rooms targeted to be decontaminated, when a conveyance distance of the mixed gas-liquid supplying pipes that the rooms targeted to be decontaminated respectively comprises is Ax, a conveyance distance of each of the corresponding decontamination solution supplying pipes is Bx, the following formula is met:

$$Ax/Bx \geq 3 \qquad (1)$$

(where x is an integer of 1 to n, and corresponds to each room targeted to be decontaminated of n rooms targeted to be decontaminated)

In addition, the present invention, according to claim 3, is directed to the decontamination system according to claim 2, characterized in that compression air to be supplied from the compressed air-generating means to the gas-liquid adjuster via the air supplying pipe is 0.05 MPa or more in ejection pressure and 5 NL/min to 70 NL/min in air flow rate, respectively, with respect to each mixed gas-liquid adjuster, and decontamination solution to be supplied from the decontamination solution-supplying means to the mixed gas-liquid adjuster via the decontamination solution supplying pipe is 0.3 mL/min to 30 mL/min in flow rate, respectively, with respect to each mixed gas-liquid adjuster.

Further, the present invention, according to claim 4, is directed to the decontamination system according to any one of claims 1 to 3, having water supplying means (70) for supplying water for humidity-controlling rooms targeted to be decontaminated (R1 to R4), the decontamination system comprising water supplying pipes (71 to 75) which respectively communicate from the water supplying means up to the mixed gas-liquid adjuster with each room targeted to be decontaminated, characterized in that, with respect to the mixed gas-liquid adjusters (31 to 35), supply of water via the water supplying pipe and supply of the decontamination solution via the decontamination solution supplying pipes (21 to 25) are switched to each other, when water is supplied to the mixed gas-liquid adjuster, a humidification mixed gas-liquid obtained by mixing the compression air and water is adjusted by the mixed gas-liquid adjusters, and the humidification mixed gas-liquid is supplied to the gas generators (41 to 45) via the mixed gas-liquid supplying pipes (61 to 65) and then the humidification mixed gas-liquid is gasified to generate humidification gas of water vapor, and when the decontamination solution is supplied to the mixed gas-liquid adjuster, a decontamination mixed gas-liquid obtained by mixing the compression air and the decontamination solution is adjusted by the mixed gas-liquid adjusters, and the decontamination mixed gas-liquid is supplied to the gas generator via the mixed gas-liquid supplying pipes and then the humidification mixed gas-liquid is gasified to generate decontamination gas.

Furthermore, a decontamination method according to the present invention, according to claim 5, is characterized by using the decontamination system according to any one of claims 1 to 3, supplying the decontamination solution to the mixed gas-liquid adjusters to thereby decontaminate an inside of each room targeted to be decontaminated by decontamination gas gasified by the gas generators.

Still furthermore, the decontamination method according to the present invention, according to claim 6, is characterized by, using the decontamination system according to claim 4, first, supplying water to the mixed gas-liquid adjusters to thereby humidity-control a humidity in each room targeted to be decontaminated, to a preset value by humidification gas gasified by the gas generators, and next, supplying the decontamination solution to the mixed gas-liquid adjuster to thereby decontaminate an inside of each room targeted to be decontaminated by decontamination gas gasified by the gas generators.

Advantageous Effects of the Invention

According to the above construction in claim 1, the decontamination solution that is a source of generation of decontamination gas is mixed with the compression air generated by compressed air-generating means and then a mixed gas-liquid is generated by the mixed gas-liquid adjusters. This mixed gas-liquid is supplied to the gas generators via the mixed gas-liquid supplying pipes and then is gasified, and decontamination gas is generated. The mixed gas-liquid is a mixture between compression air and solution and is established in a state of high density, and the conveyance speed is also high and thus a pipe of which diameter is small can be employed as a gas-liquid supplying pipe. Therefore, in a case where a plurality of rooms targeted to be decontaminated are present and an arrangement distance of the mixed gas-liquid supplying pipes with respect to the respective rooms targeted to be decontaminated is different from another one, this is an appropriate distance for each room targeted to be decontaminated, and supplying pipes of which distance is long can be arranged. By the fact, large scale equipment such as large diameter ducts is not required.

In addition, the hydrogen peroxide water in the mixed gas-liquid is established in a state of solution and thus there is no need to heat the mixed gas-liquid supplying pipes in order to prevent condensation. Therefore, even in a case where a plurality of rooms targeted to be decontaminated are present and the supplying pipes of which distance is long are arranged for each room targeted to be decontaminated, large scale equipment such as anti-condensation heaters is not required.

Further, in a case where a plurality of rooms targeted to be decontaminated are present, the compressed air-generating means and the decontamination solution-supplying means are common to each room targeted to be decontaminated, whereas the mixed gas-liquid adjusters, the gas generators, and the solution-gas mixture supplying pipes connecting these constituent elements (hereinafter, referred to as a "decontamination unit") are arranged for each room targeted to be decontaminated. By the fact, the compressed air-generating means, the decontamination solution-supplying means, and the respective gas-liquid adjusters can be arranged at positions which are spaced from the respective rooms targeted to be decontaminated. In this manner, an independent decontamination unit is arranged for each room targeted to be decontaminated, the conveyance distance of the decontamination solution supplying pipes is decreased, and the conveyance distance of the mixed gas-liquid supplying pipes is increased.

The conveyance distance of the decontamination solution supplying pipes is thus decreased, and it is possible to accurately keep track of the supply quantity of the decontamination solution relative to the mixed gas-liquid adjusters. By the fact, it is possible to accurately keep track of the amount of decontamination solution that has been supplied to the gas generators for each room targeted to be decontaminated, and the amount of decontamination gas that has been discharged to the rooms targeted to be decontaminated is identified. On the other hand, the hydrogen peroxide water in the mixed gas-liquid is established in a state of solution and does not condense and thus the conveyance distance of the mixed gas-liquid supplying pipes is increased, and the decontamination solution can be accurately conveyed distantly. Further, the hydrogen peroxide water in the pipes can be completely conveyed by compression air and thus no dead solution remains in the pipes.

Therefore, according to the present invention, there can be provided a decontamination system which does not require large scale equipment such as large diameter ducts or anti-condensation heaters, while enabling, with respect to a plurality of rooms targeted to be decontaminated as well, pipelining of which distance is long for each room, the decontamination system being capable of supplying an accurate amount of decontamination gas for each room.

In addition, according to the above constituent elements in claim 2, in each room targeted to be decontaminated, the conveyance distance Ax of the mixed gas-liquid supplying pipes may be a distance Bx of three times or more of the conveyance distance of the decontamination solution supplying pipes. By the fact, the conveyance distance of the solution-gas mixture supplying pipes is increased, and the decontamination solution can be accurately conveyed distantly. Hence, in the above construction according to claim 2 as well, the action and advantageous effects similar to those of claim 1 can be achieved more significantly.

Further, according to the above constituent elements in claim 3, it is sufficient if the compression air to be supplied to each mixed gas-liquid adjuster is 0.05 MPa or more in ejection pressure and is 5 NL/min to 70 NL/min in air flow rate. Furthermore, it is sufficient that the decontamination solution to be supplied to each mixed gas-liquid adjuster is 0.3 mL/min to 30 mL/min in flow rate. By the fact, adjustment of the mixed gas-liquid in each mixed gas-liquid adjuster and conveyance of the mixed gas-liquid via the mixed gas-liquid supplying pipes are improved. Hence, in the above construction according to claim 3 as well, the action and advantageous effects similar to those of claim 2 can be achieved more significantly.

Still furthermore, according to the above construction in claim 4, the water supplying means and the water supplying pipes are further provided, and with respect to each mixed gas-liquid adjuster, supply of water via the water supplying pipe and supply of decontamination solution via the decontamination solution supplying pipe may be switched to each other. In addition, when water has been supplied to the mixed gas-liquid adjusters, the humidification mixed gas-liquid obtained by compression air and water is adjusted by the mixed gas-liquid adjuster. This humidification mixed gas-liquid is supplied to the gas generators via the mixed gas-liquid supplying pipe and is gasified therein to generate water vapor and humidify the inside of the rooms targeted to be decontaminated. By this humidification, the humidity state in the rooms targeted to be decontaminated can be established in a more appropriate state by decontamination with decontamination gas.

On the other hand, when decontamination solution has been supplied to the mixed gas-liquid adjusters, the decontamination mixed gas-liquid obtained by mixing the compression air and the decontamination solution is adjusted by the mixed gas-liquid adjusters. This decontamination mixed gas-liquid decontaminates the rooms targeted to be decontaminated after humidity-controlled. Therefore, in the above constituent elements according to claim 4, decontamination can be carried out after humidity-control of the rooms targeted for contamination has been carried out and thus the action and advantageous effects similar to those of claim 1 can be achieved more significantly.

In addition, according to the above constituent elements in claim 5, there can be provided the decontamination method using the decontamination system according to any one of claims 1 to 3. By this fact, in the decontamination method, it is possible to attain the action and advantageous effect that are similar to those of the decontamination system according to any one of claims 1 to 3.

Further, according to the above constituent elements in claim 6, there can be provided the contamination method using the above-described contamination system according to claim 4. By the fact, in the decontamination method, it is possible to attain the action and advantageous effects that are similar to those of the decontamination system according to claim 4.

DESCRIPTION OF EMBODIMENTS

Hereinafter, embodiments of decontamination systems according to the present invention will be described. Incidentally, the present invention is not limited to the embodiments shown below.

First Embodiment

Figure 1:
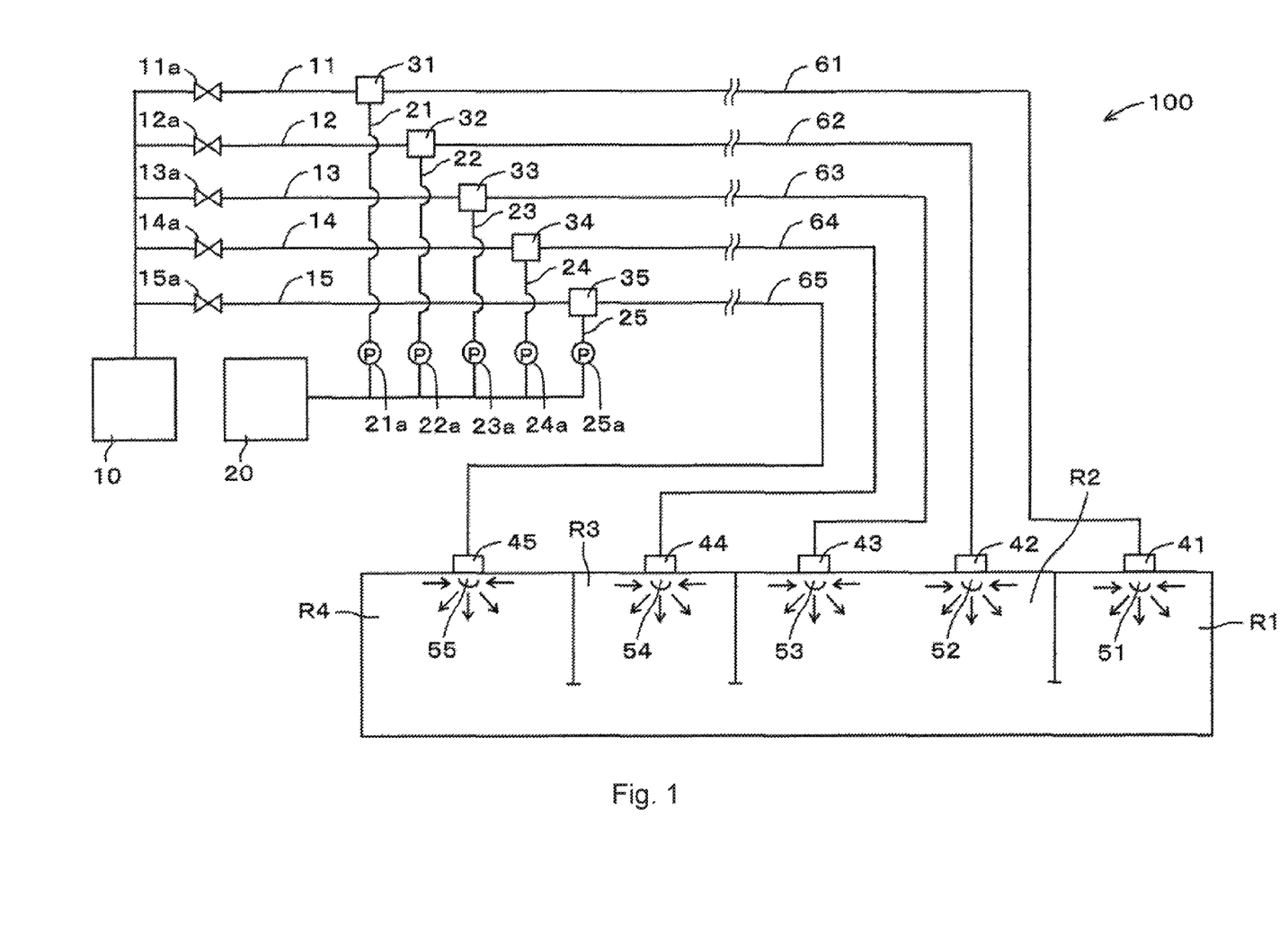
FIG. 1 is a schematic structural view of a decontamination system according to a first embodiment.

First, a first embodiment of a decontamination system according to the present invention will be described with reference to the drawings. FIG. 1 is a schematic structural view of a decontamination system 100 according to the first embodiment. In the first embodiment, as shown in FIG. 1, four sterile rooms (clean rooms) of which areas are different from each other are rooms targeted to be decontaminated R1 to R4. Among the respective rooms targeted to be decontaminated, doors are respectively provided, it may be that these doors are decontaminated in an open state, or alternatively, these doors are decontaminated in a closed state. Incidentally, in the first embodiment, at the time of decontamination, these doors are decontaminated in the open state.

In FIG. 1, the decontamination system 100 has: an air compressor 10 and a hydrogen peroxide water tank 20 which are common to each of the rooms targeted to be decontaminated R1 to R4. Also, the rooms targeted to be decontaminated R1 to R4 are provided with ejectors 31 to 35, evaporators 41 to 45, and circulating fans 51 to 55 respectively correspond to each room.

The air compressor 10 acts as compressed air-generating means for generating compression air as carrier gas for conveying hydrogen peroxide water. This air compressor 10 is arranged at a position which is spaced from the rooms targeted to be decontaminated R1 to R4.

The hydrogen peroxide water tank 20 acts as decontamination solution-supplying means for reserving hydrogen peroxide water which is a source of generation of hydrogen peroxide gas as contamination gas. This hydrogen peroxide water tank 20 is arranged in the vicinity of the pneumatic compressor 10 at a position which is spaced from each of the rooms targeted to be decontaminated R1 to R4. Here, although the contamination of the hydrogen peroxide water to be reserved in the hydrogen peroxide water tank 20 is not limited in particular, in general, it is preferable to use the water of 30 to 35% by weight in consideration of handling of a hazardous matter or the like.

Ejectors 31 to 35 act as mixed gas-liquid adjusters for adjusting the mixture mist obtained by mixing hydrogen peroxide water in compression air. These ejectors 31 to 35 are arranged in the air compressor 10 and the hydrogen peroxide water tank 20 at positions which are spaced from the rooms targeted to be decontaminated R1 to R4.

Evaporators 41 to 45 act as gas generators to gasify the mixture mist including hydrogen peroxide water conveyed from the ejectors 31 to 35 to generate mixture gas of hydrogen peroxide and water vapor (hereinafter, referred to as "hydrogen peroxide gas"). These evaporators 41 to 45 have a heated evaporation plate and evaporate the supplied mixture mist. Although it is sufficient if a temperature of the evaporation plate has an enough heat rate to perform gasification, in general, it is sufficient if the temperature is of the order of 110 to 200° C. These evaporators 41 to 45 are arranged outside of the exterior walls of the rooms targeted to be decontaminated R1 to R4.

The circulating fans 51 to 55 uniformly circulates the hydrogen peroxide gas that is discharged from the evaporators 41 to 45 in the rooms targeted to be decontaminated R1 to R4. These circulating fans 51 to 55 are arranged in the respective rooms targeted to be decontaminated at the lower part of the evaporators 41 to 45. The hydrogen peroxide gas that is discharged from ejection openings of the evaporators 41 to 45 is supplied to blowout openings of the circulating fans 51 to 55, and circulates in each room targeted to be decontaminated.

Incidentally, in the largest room targeted to be decontaminated R2, there are arranged: two sets of decontamination units (two ejectors 32, 33, two evaporators 42, 43, and two mixture mist pipes 62, 63 which will be described later); and two circulating fans 52, 53. This is because the capacity of the room targeted to be decontaminated R2 is large, and the decontamination efficiency is made higher by discharging hydrogen peroxide gas from two openings while being divided into two sets of decontamination units than by supplying a large amount of hydrogen peroxide gas from only one set of decontamination units. Also, depending on an area of a room targeted to be decontaminated, many more decontamination units than two sets thereof may be provided in one room. Incidentally, even in a case where a plurality of decontamination units are thus provided in one room, there may be small distance pipes, and there is no problem in terms of equipment costs.

In addition, in FIG. 1, the decontamination system 100 is provided with: air pipes 11 to 15 which communicate with the air compressor 10 and the ejectors 31 to 35; hydrogen peroxide water pipes 21 to 25 which communicate with the hydrogen peroxide water tank 10 and the ejectors 31 to 35; and mixture mist pipes 61 to 65 which communicate with the ejectors 31 to 35 and the evaporators 41 to 45.

The air pipes 11 to 15 communicate with an ejection opening of the air compressor 10 and driving flow paths of the ejectors 31 to 35 (not shown). In the pipelines of the air pipes 11 to 15, switching valves 11a to 15a to control supplying of compression air are respectively provided. Here, materials for, and the pipe diameters of, the air pipes 11 to 15 are not limited in particular, in general, a stainless steel of which inner diameter is 1 to 10 mm is preferred. Incidentally, although not shown in FIG. 1, in the pipeline between the air compressor 10 and the air pipes 11 to 15, an air driver, an air regulator, an auto drain, an oil mist separator or any other filters may be provided without being limited thereto.

The hydrogen peroxide water pipes 21 to 25 communicate with a supply opening of the hydrogen peroxide water tank 20 and a suction flow paths (not shown) of ejectors 31 to 35. In the pipelines of the hydrogen peroxide water pipes 21 to 25, tube pumps 21a to 25a to control supplying of hydrogen peroxide water are provided. Here, although the material for, and pipe diameters of, the hydrogen peroxide water pipes 21 to 25 are not limited in particular as long as they can be used for hydrogen peroxide water, in general, a stainless steel of which inner diameter is 1 to 10 mm is preferable.

The mixture mist pipes 61 to 65 respectively communicate with the ejection flow paths of the ejectors 31 to 35 and the evaporators 41 to 45. The mixture mist pipes 61 to 65 are laid out at a long distance from the vicinity of the pneumatic compressor 10 and the hydrogen peroxide water tank 20 up to the positions of the evaporators 41 to 45 that have been arranged outside of the top walls of the rooms targeted to be decontaminated R1 to R4. Here, it is preferable that the materials for, and the pipe diameters of, the mixture mist pipes 61 to 65 be enough to convey, at a long distance, a necessary amount per unit time; and in general, a stainless pipe of which inner diameter is 1 to 10 mm is preferable.

Thus, with respect to the rooms targeted to be decontaminated R1 to R4, the air pipes 11 to 15, the hydrogen peroxide water pipes 21 to 25, and the mixture mist pipes 61 to 65 are respectively arranged, whereby hydrogen peroxide gas can be independently for each room targeted to be decontaminated, and accurate decontamination can be carried out for each room.

In addition, as is obvious from FIG. 1, the conveyance distance of the mixture mist pipes 61 to 65 is longer than the conveyance distance of the air pipes 11 to 15 or the conveyance distance of the hydrogen peroxide water pipes 21 to 25. Although the conveyance distance of the mixture mist by the mixture mist pipes 61 to 65 is not limited in particular, in general, the order of 3 to 100 m can be conveyed. On the other hand, the conveyance distance of the air pipes 11 to 15 or the conveyance distance of the hydrogen peroxide pipes 21 to 25 can be reduced.

In the present invention, when the conveyance distance of the mixture mist pipes 61 to 65 is Ax, and the conveyance distance of the hydrogen peroxide water pipes 21 to 25 is Bx (x is an integer of 1 to n, and corresponds to each room targeted to be decontaminated of n rooms targeted to be decontaminated), it may be that the value of (Ax/Bx) is 3 or more, or alternatively, 5 or more and further 10 or more as required. Thus, the conveyance distance of the mixture mist pipes 61 to 65 is made longer than the conveyance distance of the hydrogen peroxide water pipes 21 to 25, and the hydrogen peroxide water can be stably conveyed in a state of mixture mist even at a long distance from the position of the hydrogen peroxide water tank 20 to each room targeted to be decontaminated.

In the first embodiment, the mixture mixt is a mixture between compression air and hydrogen peroxide water, is established in a state of high density, and high in conveyance speed; and therefore, pipes of which diameters are respectively small can be employed as the mixture mist pipes 61 to 65. Therefore, the mixture mist pipes 61 to 65 can be arranged at a long distance for each room targeted to be decontaminated. By the fact, large scale equipment such as large diameter ducts is not required.

In addition, the hydrogen peroxide water in the mixture mixt is established in a state of solution and thus there is no need to heat the mixture mist pipes 61 to 65 in order to prevent condensation. Therefore, even in a case where pipes are arranged at a long distance for each room targeted to be decontaminated, large scale equipment such as anti-condensation heaters is not required.

Thus, the conveyance distance of the hydrogen peroxide water pipes 21 to 25 is reduced, and it is possible to accurately keep track of the supply quantity of hydrogen peroxide water to the ejectors 31 to 35. By the fact, it is possible to accurately keep track of the amount of hydrogen peroxide water that has been supplied to the evaporators 41 to 45 for each room targeted to be decontaminated, and the amount of hydrogen peroxide water that has been discharged to the room targeted to be decontaminated can be identified. On the other hand, the hydrogen peroxide water in the mixture mist is established in a state of solution and does not condense and thus the conveyance distance of the mixture mist pipes 61 to 65 is increased, and the hydrogen peroxide water can be accurately conveyed distantly. Further, the hydrogen peroxide water in the mixture mist pipes 61 to 65 can be completely conveyed by compression air and thus no dead solution remains in the pipes.

Next, a decontamination method for decontaminating rooms targeted to be decontaminated R1 to R4 by using the decontamination system 100 according to the first embodiment will be described.

In the first embodiment, four rooms targeted to be decontaminated R1 to R4 are decontaminated at a same gas generation time. Since an area of each room targeted to be decontaminated is different, the amount of hydrogen peroxide gas to be discharged per unit time for each room targeted to be decontaminated is computed. From these amounts of discharged gas, the amount of hydrogen peroxide water supplied from the hydrogen peroxide water tank 20 via the hydrogen peroxide water pipes 21 to 25 is computed with respect to the ejectors 31 to 35 that correspond to each room targeted to be decontaminated. Incidentally, it is preferable that each room before decontaminated be set in a predetermined condition by employing a temperature controller and a humidity controller.

Next, a decontamination operation is started. First, switching valves 11*a* to 15*a* of the air pipes 11 to 15 are opened, and compression air is supplied from the air compressor 10 via the air pipes 11 to 15 to the driving flow paths of the ejectors 31 to 35. Here, it is preferable that the compression air to be supplied to the ejectors 31 to 35 be 0.05 MPa or more in ejection pressure and 5 to 70 NL/min in air flow rate, respectively. It is preferable that the air flow rate be appropriately set according to the concentration and amount of hydrogen peroxide water to be supplied to each room targeted to be decontaminated and a distance to each room targeted to be decontaminated.

Next, the tube pumps 21*a* to 25*a* of the hydrogen peroxide water pipes 21 to 25 are actuated, and hydrogen peroxide water is supplied from the hydrogen peroxide water tank 20 via the hydrogen peroxide water pipes 21 to 25 to the suction flow paths of the ejectors 31 to 35. Incidentally, the supply amount of the hydrogen peroxide water corresponds to the amount computed, as described above, with respect to the ejectors 31 to 35. Here, although the concentration of the hydrogen peroxide water to be supplied to the ejector 31 to 35 is not limited in particular, the one of 30 to 35% by weight generally available may be used as it is, or alternatively, may be used by condensing or diluting it. Also, it is preferable that the hydrogen peroxide water to be supplied to the ejectors 31 to 35 be 0.3 to 30 mL/min at flow rate, or alternately, the flow rate may be adjusted to 0.5 to 15 mL/min, respectively.

Incidentally, the amount of hydrogen peroxide water is in the above range and the amount of compression air is in the above range, and the mixture mist obtained by mixing hydrogen peroxide water can be thereby conveyed even at a long distance via the mixture mist pipes 61 to 65.

By means of the operation described above, in the ejectors 31 to 35, the hydrogen peroxide water and the compression air change to mixture mist, and the mixture mixt is supplied from the ejection flow paths of the ejectors 31 to 35 via the mixture mist pipes 61 to 65 to the evaporators 41 to 45.

In the evaporators 41 to 45, the mixture mist evaporates and then hydrogen peroxide gas is generated. The hydrogen peroxide gas gasified in the evaporators 41 to 45 is supplied from the ejection openings of the evaporators 41 to 45 to the blowout openings of the circulating fans 51 to 55 that have been installed in the rooms targeted to be decontaminated R1 to R4. By the fact, the hydrogen peroxide gas is discharged into each room targeted to be decontaminated and then the inside of each room targeted to be decontaminated is uniformly decontaminated.

In this manner, the hydrogen peroxide gas is discharged for a predetermined period of time. At a stage at which the predetermined period of time has elapsed, the tube pumps 21$a$ to 25$a$ of the hydrogen peroxide water pipes 21 to 25 are stopped, and supply of the hydrogen peroxide water is stopped. At this stage, the compression air is supplied to the ejectors 31 to 35 via the air pipes 11 to 15, and in this state, all of the remaining hydrogen peroxide water in the mixture mist pipes 61 to 65 is supplied to the evaporators 41 to 45. By the fact, to the rooms targeted to be decontaminated R1 to R4, the predetermined amounts of peroxide water are accurately discharged, respectively.

Next, the switching valves 11$a$ to 15$a$ of the air pipes 11 to 15 are closed, and supply of the compression air is stopped. Afterwards, the hydrogen peroxide gas in each room is discharged, airing of the inside of the room is performed, and the decontamination operation is completed. Incidentally, it is preferable that each of the operations be carried out by means of automatic control with the use of a microcomputer.

Second Embodiment

Figure 2:
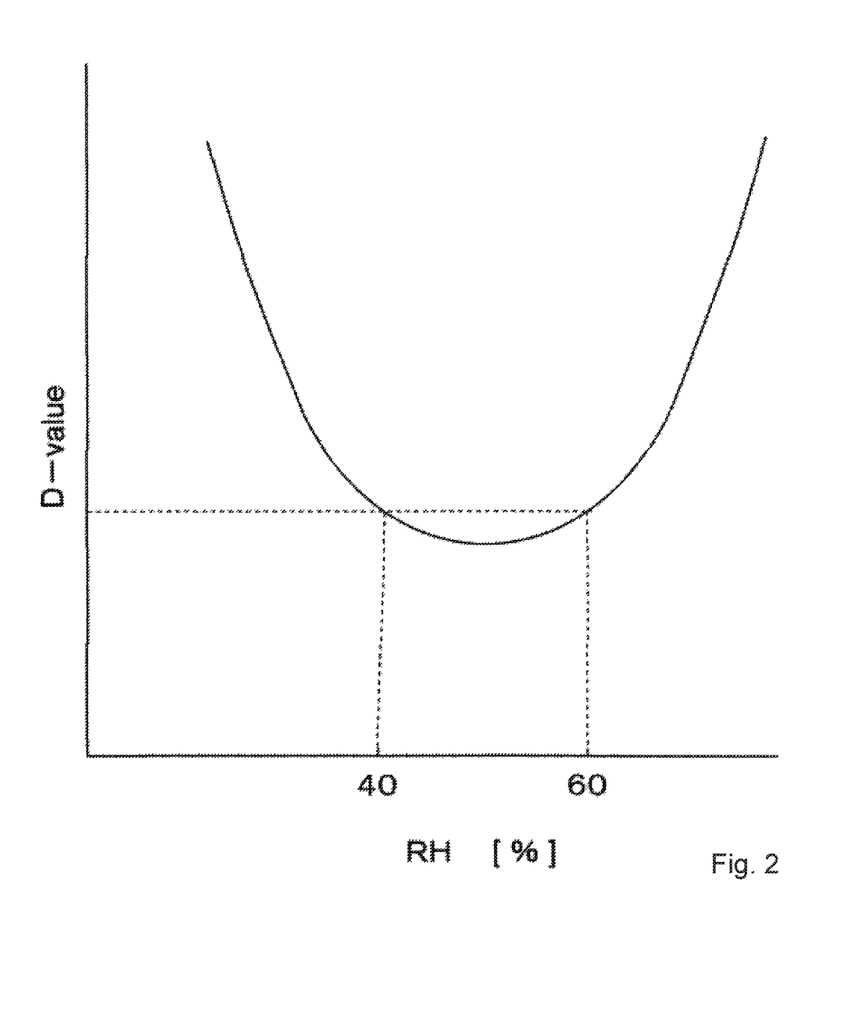
FIG. 2 is a schematic diagram showing a relationship between a decontamination effect (D-value) exerted by hydrogen peroxide gas and a relative humidity in room at that juncture.

Next, a second embodiment of a decontamination system according to the present invention will be described. The second embodiment is directed to a decontamination system which is capable of carrying out humidity-control in each room targeted to be decontaminated prior to decontamination exerted by hydrogen peroxide gas. In the decontamination exerted by hydrogen peroxide, the temperature and humidity in room at the time of decontamination, in particular, the humidity condition is important. FIG. 2 is a schematic diagram showing a relationship between a decontamination effect (D value) exerted by the hydrogen peroxide gas and the relative humidity in room at that juncture. As shown in FIG. 2, in the decontamination exerted by the hydrogen peroxide gas, it is found that the decontamination effect is high (the D value is low) when the relative humidity in room is 40 to 60%.

Here, the D value (Decimal reduction value) means time (minutes) required to reduce the initial bacteria count to $\frac{1}{10}$ (90% extinction) under a predetermined decontamination condition. The lower D value is, the shorter time decontamination can be carried out, and the higher the decontamination effect is.

Figure 3:
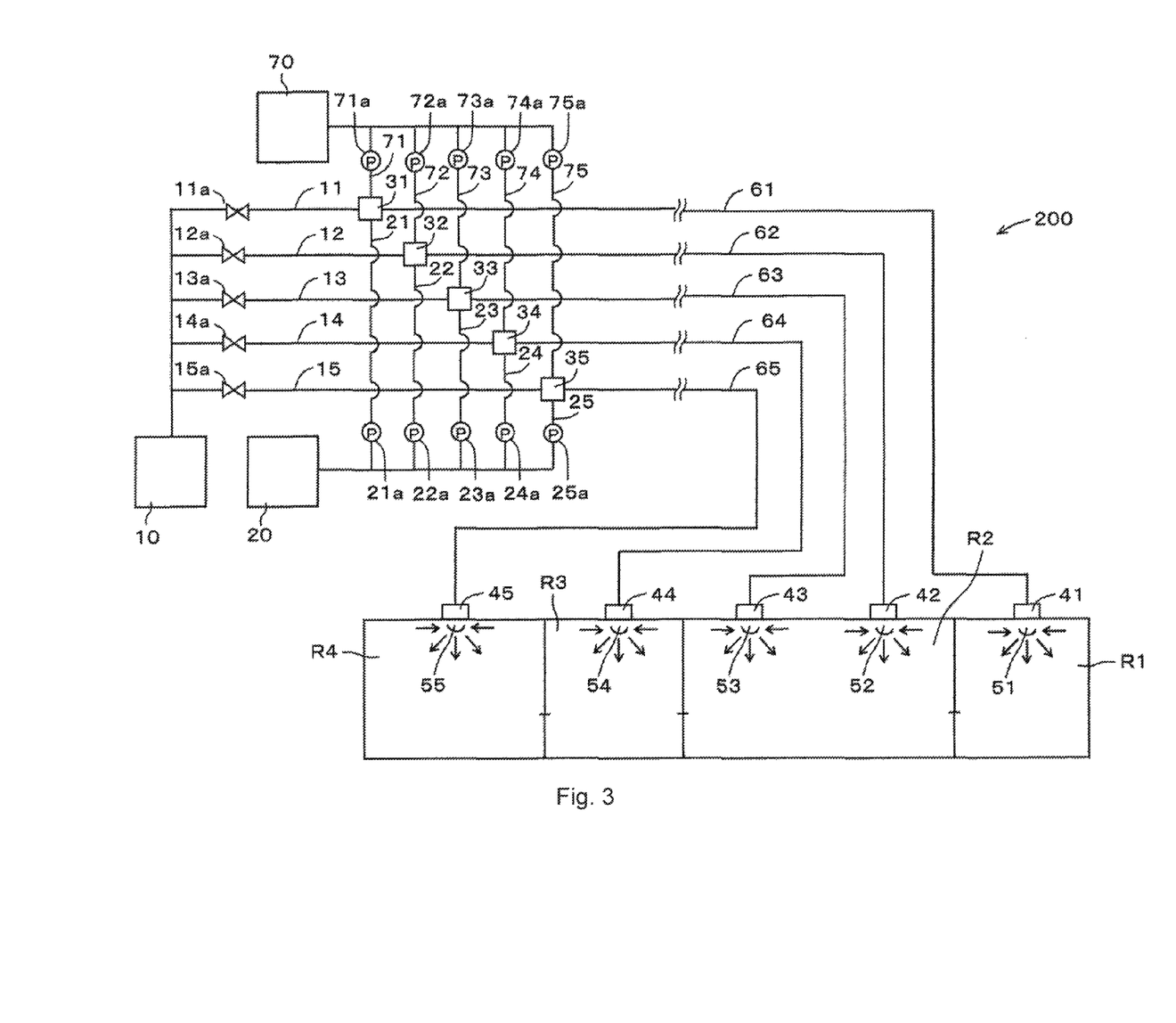
FIG. 3 is a schematic structural view of a decontamination system according to a second embodiment.

The second embodiment of the decontamination system according to the present invention will be described with reference to the drawings. FIG. 3 is a schematic structural view of a decontamination system 200 according to the second embodiment. In the second embodiment, like the first embodiment, four sterile rooms (clean rooms) of which areas are different from each other are rooms targeted to be decontaminated R1 to R4. Between the respective rooms targeted to be decontaminated, doors are respectively provided, and it may be that these doors are decontaminated in an open state, or alternatively, are decontaminated in a closed state. Incidentally, in the second embodiment, humidification and decontamination were carried out in the state in which all of these doors were closed.

In FIG. 3, the decontamination system 200 has a pneumatic compressor 10, a hydrogen peroxide tank 20, and a distilled water tank 70 which are common to rooms targeted to be decontaminated R1 to R4. Also, the rooms targeted to be decontaminated R1 to R4 are respectively provided with: ejectors 31 to 35, evaporators 41 to 45, and circulating fans 51 to 55 corresponding to each room.

In the second embodiment, a construction of the air compressor 10 and the hydrogen peroxide water tank 20 is similar to that of the first embodiment, and a duplicate description thereof is omitted.

In the second embodiment, unlike the first embodiment, a distilled water tank 70 is included. The dilute tank 70 acts as distilled water supplying means for reserving distilled water which is a source of generation of water vapor for humidity-controlling the inside of rooms targeted to be decontaminated. The distilled water tank 70 is arranged in the vicinity of the pneumatic compressor 10 and the hydrogen peroxide water tank 20 at a position which is spaced from the rooms targeted to be decontaminated R1 to R4.

The ejectors 31 to 35, like the first embodiment, respectively acts as mixed gas-liquid adjusters for adjusting the mixture mist (the decontamination mixed gas-liquid) obtained by mixing hydrogen peroxide water in compression air, and also, acts as mixed gas-liquid adjusters for adjusting the mixture mist (the humidification mixed gas-liquid) obtained by mixing distilled water in compression air. Thus, in the second embodiment, in suction flow paths (not shown) of the ejectors 31 to 35, switching valves (not shown) are respectively provided so that solution can be supplied from the two paths.

One path is similar to that of the first embodiment, and communicates with the suction flow paths of the ejectors 31 to 35 and the hydrogen peroxide water tank 70. The other path communicates with the suction flow paths of the ejectors 31 to 35 and the distilled water tank 70. The ejectors 31 to 35 are provided in the vicinity of the pneumatic compressor 10, the hydrogen peroxide water tank 20 and the distilled water tank 70 at positions from the rooms targeted to be decontaminated R1 to R4.

The evaporators 41 to 45 respectively acts as gas generators to gasify the mixture mist including the distilled water or hydrogen peroxide water conveyed from the ejectors 31 to 35 and then change to water vapor or hydrogen peroxide gas. In the second embodiment, the evaporators 41 to 45 each having a similar evaporation plate to that of the first embodiment are employed.

The circulating fans 51 to 55 uniformly circulate the water vapor or hydrogen peroxide gas discharged from the evaporators 41 to 45 in the rooms targeted to be decontaminated R1 to R4. In the second embodiment, like the first embodiment, the circulating fans 51 to 55 are respectively arranged in the rooms targeted to be decontaminated at the lower parts of the evaporators 41 to 45. The water vapor or hydrogen peroxide gas that is discharged from ejection openings of the evaporators 41 to 45 is supplied to the blowout openings of the circulating fans 51 to 55, and circulates in each room targeted to be decontaminated.

Incidentally, in the second embodiment as well, in the room targeted to be decontaminated R2 that is the largest room, there are arranged: two sets of decontamination units (two ejectors 32, 33, two evaporators 42, 43, and two mixture mist pipes 62, 63); and two circulating fans 52, 53. This is because the capacity of the room targeted to be decontaminated R2 is large, and the humidity-control efficiency and decontamination effect are higher by discharging hydrogen peroxide gas from two openings while being divided into two sets of decontamination units than by supplying a large amount of hydrogen peroxide gas from only one set of decontamination units. Also, dependent on the area of a room targeted to be decontaminated, more decontamination units than two sets may be provided in one room. Incidentally, even in a case a plurality of decontamination units are thus provided, there may be pipes of which diameters are respectively small, and there is no problem in terms of equipment costs.

In addition, in FIG. 3, the decontamination system 200 is provided with: air pipes 11 to 15 which communicate with the pneumatic compressor 10 and the ejectors 31 to 35; hydrogen peroxide water pipes 21 to 25 which communicate with the hydrogen peroxide water tank 20 and the ejectors 31 to 35; distilled water pipes 71 to 75 which communicate with the distilled water tank 70 and the ejectors 31 to 35; and mixture mist pipes 61 to 65 which communicate with the ejectors 31 to 35 and the evaporators 41 to 45.

In the second embodiment, a construction of the air pipes 11 to 15, the hydrogen peroxide water pipes 21 to 25, and the mixture mist pipes 61 to 65 is similar to that of the first embodiment, and a duplicate description thereof is omitted.

The distilled water pipes 71 to 75 communicates with a supply opening of the distilled water tank 70 and suction flow paths (not shown) of the ejectors 31 to 35. In the suction flow paths each, as described above, a switching valve (not shown) is provided, and two paths are provided. In the pipelines of the distilled water pipes 71 to 75, tube pumps 71a to 75a to control supplying of hydrogen peroxide water are respectively provided. Here, although the material for, and a pipe diameter of, the distilled water pipes 71 to 75 are not limited in particular, in general, a stainless pipe of which inner diameter is 1 to 10 mm is preferable.

Thus, with respect to the rooms targeted to decontamination R1 to R4, the air pipes 11 to 15, the hydrogen peroxide water pipes 21 to 25, the distilled water pipes 71 to 75, and the mixture mist pipes 61 to 65 are respectively arranged, whereby water vapor and hydrogen peroxide gas can be independently discharged for each room targeted to be decontaminated, and accurate humidity-control and decontamination can be carried out for each room.

In addition, as is obvious from FIG. 3, the conveyance direction of the mixture mixt pipes 61 to 65 is longer than the conveyance direction of the air pipes 11 to 15, the conveyance distance of the hydrogen peroxide water pipes 21 to 25, or the conveyance distance of the distilled water pipes 71 to 75. Although the conveyance distance of the mixture mixt by the mixture mist pipes 61 to 65 is not limited in particular, in general, the order of 3 to 100 m can be conveyed. On the other hand, the conveyance distance of the air pipes 11 to 15, the conveyance distance of the hydrogen peroxide water pipes 21 to 25, or the conveyance distance of the distilled water pipes 71 to 75 can be reduced.

In the second embodiment, the mixture mist is a mixture of compression air and distilled water or hydrogen peroxide water, is established in a state of high density, and is high in conveyance speed; and therefore, pipes of which diameters are respectively small can be employed as the mixture mist pipes 61 to 65. Therefore, the mixture mist pipes 61 to 65 can be arranged at a long distance for each room targeted to be decontaminated. By the fact, large scale equipment such as large diameter ducts is not required.

In addition, the distilled water or hydrogen peroxide water in the mixture mist is established in a state of solution and thus there is no need to heat the mixture mist pipes 61 to 65 in order to prevent condensation. Therefore, even in a case where pipes of which distance is long are arranged for each room targeted to be decontaminated, large scale equipment such as anti-condensation heaters is not required.

Thus, by reducing the conveyance distance of the hydrogen peroxide water pipes 21 to 25, it is possible to accurately keep track of the supply amount of hydrogen peroxide water to the ejectors 31 to 35. By the fact, it is possible to accurately keep track of the amount of hydrogen peroxide water that has been supplied to the evaporators 41 to 45 for each room targeted to be decontaminated, and the amount of hydrogen peroxide gas that has been discharged to the room targeted to be decontaminated is identified.

On the other hand, the hydrogen peroxide water in the mixture mist is established in a state of solution and does not condense and thus the conveyance distance of the mixture mist pipes 61 to 65 is increased, and the hydrogen peroxide water can be accurately conveyed distantly. Further, the hydrogen peroxide water in the mixture mist pipes 61 to 65 can be completely conveyed by compression air and thus no dead solution remains in the pipes.

Next, a decontamination method for humidity-controlling and then decontaminating the room targeted to be decontaminated R1 to R4 by using the decontamination system 200 according to the second embodiment will be described.

In the second embodiment, first, the relative humidity of the rooms targeted to be decontaminated R1 to R4 is humidity-controlled at a predetermined value. As described above, it is preferable that the relative humidity in room be 40 to 60%. However, as described above, water vapor is included in the hydrogen peroxide gas to be discharged into room by means of decontamination, and the humidity in room rises with the elapse of decontamination time. Therefore, the relative humidity at the time of start of decontamination may be slightly lower than 40% so that the time during which the relative humidity is maintained at 40 to 60% is the longest from the time of start of decontamination up to the time of completion thereof.

First, a humidity-control operation is started. The switching valves 11a to 15a of the air pipes 11 to 15 are opened, and compression air is supplied from the pneumatic compressor 10 via the air pipes 11 to 15 to the driving flow paths of the ejectors 31 to 35. Here, the ejection pressure and air flow rate of the compression air to be supplied to the ejectors 31 to 35 are similar to those of the compression air in decontamination operation of the first embodiment.

Next, the tube pumps 71a to 75a of the distilled water pipes 71 to 75 are actuated, and distilled water is supplied from the distilled water tank 70 via the distilled water pipes 71 to 75 to the suction flow paths of the ejectors 31 to 35. At this time, the suction flow paths of the ejectors 31 to 35 need to be set to the distilled water pipes 71 to 75 sides by switching of the switching valves (not shown). Here, the amount of distilled water to be supplied to the ejectors 31 to 35 may be the same order of the amount of hydrogen peroxide water in decontamination operation of the first embodiment.

By means of the operation described above, in the ejectors 31 to 35, distilled water and compression air change to gas-liquid mist, and the resultant mist is supplied from the ejection flow paths of the ejectors 31 to 35 via the mixture mist pipes 61 to 65 to the evaporators 41 to 45.

In the evaporators 41 to 45, the mixture mist evaporates and then water vapor is generated. The water vapor that is gasified in the evaporators 41 to 45 is supplied from the ejection openings of the evaporators 41 to 45 to the blowout openings of the circulating fans 51 to 55 that have been installed in the rooms targeted to be decontaminated R1 to R4. By the fact, the water vapor is discharged into each room targeted to be decontaminated, and the inside of each room targeted to be decontaminated is uniformly humidity-controlled.

Here, in each of the rooms targeted to be decontaminated R1 to R4, a temperature sensor and a humidity sensor (both of which are not shown) are installed. When the temperature and relative humidity of the rooms targeted to be decontaminated R1 to R4 are in the set range with elapse of humidity-control operation, the tube pumps 71a to 75a of the distilled water pipes 71 to 75 are stopped, and supply of the distilled water is stopped. At this stage, compression air is supplied to each of the ejectors 31 to 35 via the air pipes 11 to 15, and in this state, all of the remaining distilled water in the mixture mist pipes 61 to 65 is delivered to the evaporators 41 to 45.

Incidentally, in order to ensure that the relative humidity of each room targeted to be decontaminated is in the set range, a time lag occurs for each room. Therefore, the relative humidity needs to be individually controlled for each room. Once the relative humidity of the room targeted to be decontaminated in the set range has decreased, supply of the distilled water is started again, and humidity-control operation is completed at a time point at which the relative humidity of all of the rooms has been in the set range.

Next, a decontamination operation is started. In the second embodiment as well, four rooms targeted to be decontaminated R1 to R4 are decontaminated at a same gas generation time. Computation of the amount of hydrogen peroxide gas to be discharged per unit time for each room targeted to be decontaminated and the amount of the amount of hydrogen peroxide water to be supplied from the hydrogen peroxide tank 20 via the hydrogen peroxide pipes 21 to 25 to the ejectors 31 to 35 is similar to that of the first embodiment.

Next, the decontamination operation is started. The switching valves 11a to 15a of the air pipes 11 to 15 are opened, and compression air is supplied from the pneumatic compressor 10 via the air pipes 11 to 15 to the driving flow paths of the ejectors 31 to 35. Here, the ejection operation and air flow rate of compression air to be supplied to each of the ejectors 31 to 35 are similar to those of compression air in decontamination operation of the first embodiment.

Next, switch values (not shown) of the suction flow paths of the ejectors 31 to 35 are set to the hydrogen peroxide waters 21 to 25 sides by switching them. Afterwards, the tube pumps 21a to 25a of the hydrogen peroxide water pipes 21 to 25 are actuated, and hydrogen peroxide water is supplied from the hydrogen peroxide water tank 20 via the hydrogen peroxide water pipes 21 to 25 to the suction flow paths of the ejectors 31 to 35. Here, the hydrogen peroxide water to be supplied to the ejector 31 is similar to the amount of hydrogen peroxide water in decontamination operation of the first embodiment. Incidentally, the supply amount of the hydrogen peroxide water corresponds to the computed amount, as described above, with respect to the ejectors 31 to 35.

By means of the operation described above, in the ejectors 31 to 35, the hydrogen peroxide water and the compression air change to gas-liquid mist, and the resultant mist is supplied from the ejection flow paths of the ejectors 31 to 35 via the mixture mist pipes 61 to 65 to the evaporators 41 to 45.

In the evaporators 41 to 45, the mixture mist evaporates and then hydrogen peroxide gas is generated. The water vapor that has been gasified in the evaporators 41 to 45 is supplied from the ejection openings of the evaporators 41 to 45 to the blowout openings of the circulating fans 51 to 55 that have been installed in the rooms targeted to be decontaminated R1 to R4. By the fact, the water vapor is discharged into each room targeted to be decontaminated, and the inside of each room targeted to be decontaminated is uniformly humidity-controlled.

In this manner, the hydrogen peroxide gas is discharged during a predetermined period of time. At a stage at which the predetermined period of time has elapsed, the tube pumps 21a to 25a of the hydrogen peroxide water pipes 21 to 25 are stopped, and supply of the hydrogen peroxide water is stopped. At this time, the compression air is supplied to the ejectors 31 to 35 via the air pipes 11 to 15, and in this state, all of the hydrogen peroxide water that remains in the mixture mist pipes 61 to 65 is delivered to the evaporators 41 to 45. By the fact, a predetermined amount of hydrogen peroxide gas is accurately discharged to the rooms targeted to be decontaminated R1 to R4.

Next, the switching valves 11a to 15a of the air pipes 11 to 15 are closed, and supply of the compression air is stopped. Afterwards, the hydrogen peroxide gas in room is discharged, aeration in room is carried out, and decontamination operation is completed. Incidentally, it is preferable that each of the above operations be carried out by means of automatic control with the use of microcomputer.

Hereinafter, based on the embodiments described above, the following decontamination operations of Examples were respectively carried out.

Example 1

Example 1 was carried out based on the first embodiment. Incidentally, in the Example 1, rooms targeted to be decontaminated, of which capacities were different from those of the first embodiment described with reference to FIG. 1, were decontaminated. The rooms targeted to be decontaminated in the Example 1 are four large and small clean rooms in medical and pharmaceutical manufacturing line, and the capacity of each room is shown in Table 1. In particular, the capacity of a fourth room was 258 m$^3$, and it was very large. To these rooms targeted to be decontaminated, the decontamination system according to the first embodiment was applied. The number of decontamination units that were arranged with respect to each room is shown in Table 1. As to the fourth room of which capacity is large, five sets of decontamination units were arranged.

In the Example 1, stainless pipes (SUS304) of which inner diameter is 6 mm were used as mixture mist pipes. The values of (Ax/Bx) representative of a ratio between the conveyance distance Ax of the mixture mist pipes and the conveyance distance Bx of the hydrogen peroxide water pipes was 3.5 to 13, as shown in Table 1. Thus, in the Example 1, the conveyance distance of the mixture mist pipes to convey the mixture mist of hydrogen peroxide water was long.

Next, 6-algorithm reduction BI of which number is required to check the decontamination effect was set at a predetermined position of each room. Incidentally, in the Example 1, all of doors between the respective rooms were opened. Also, although humidity-control of each room was not carried out in particular, the room temperature was about 25° C. and the relative humidity was about 35% for each room. From this state, decontamination operation along the first embodiment was carried out, and with respect to all of the rooms, a necessary amount of hydrogen peroxide gas was discharged over a predetermined period of time.

The room temperature of each room after completion of decontamination operations was about 30° C., and the relative humidity at that time was about 55%. In order to remove the hydrogen peroxide gas from each room targeted to be decontaminated, after discharge of the hydrogen peroxide gas had been stopped, airing in room was carried out and thereafter all the BI was re-collected.

TABLE 1

| TARGET ROOM NO. | CAPACITY ($m^3$) | DECONTAMINATION UNIT NO. | CONVEYANCE DISTANCE (m) | | | Ax/Bx | DECONTAMINATION EFFECT |
| | | | MIST LINE (AX) | $H_2O_2$ LINE (BX) | AIR LINE | | |
|---|---|---|---|---|---|---|---|
| 1 | 12 | 1 | 7 | 2 | 1 | 3.5 | $10^{-6}$ |
| 2 | 120 | 2 | 11 | 2 | 1 | 5.5 | $10^{-6}$ |
| | | 3 | 13 | 2 | 1 | 6.5 | |
| 3 | 83 | 4 | 9 | 2 | 1 | 4.5 | $10^{-6}$ |
| | | 5 | 11 | 2 | 1 | 5.5 | |
| 4 | 258 | 6 | 18 | 2 | 1 | 9 | $10^{-6}$ |
| | | 7 | 19 | 2 | 1 | 9.5 | |
| | | 8 | 23 | 2 | 1 | 11.5 | |
| | | 9 | 24 | 2 | 1 | 12 | |
| | | 10 | 26 | 2 | 1 | 13 | |

The re-collected BI was cultured by a predetermine method and then the degree of sterilization was determined. In the Example 1, the used BI is for 6-algorithm reduction, and determination was made assuming that 6-algorithm reduction was achieved as the condition that the sterilization indicator bacteria of all the re-collected BI were lethal. In the field of decontamination effect in Table 1, achievement of 6-algorithm reduction was represented as "$10^{-6}$". As is obvious from Table 1, in all of the rooms targeted to be decontaminated, 6-algorithm reduction was achieved, and in particular, the capacity of a fourth room was 313 $m^3$, and it was very large. To these rooms targeted to be decontaminated, the decontamination system according to the second embodiment was applied. The number of decontamination units that were arranged with respect to each room is shown in Table 2. As to the third room of which capacity is large, six sets of decontamination units were arranged.

In the Example 2, stainless pipes (SUS304) of which inner diameter is 6 mm were used as mixture mist pipes. The values of (Ax/Bx) representative of a ratio between the conveyance distance Ax of the mixture mist pipes and the conveyance distance Bx of the hydrogen peroxide water pipes was 3 to 18.5, as shown in Table 2. Thus, in the Example 2, the conveyance distance of the mixture mist pipes to convey the mixture mist of hydrogen peroxide water was long.

Next, 6-algorithm reduction BI of which count is required to check the decontamination effect was set at a predetermined position of each room. Incidentally, in the Example 2, all of doors among the respective rooms were closed. Next, humidity control operation was carried out along the second embodiment, and in each room, at the temperature range of 26 to 28° C., the relative humidity was humidity-controlled to about 40%. Next, decontamination operation was carried out along the second embodiment, and in all of the rooms, a necessary amount of hydrogen peroxide gas was discharged over a predetermined period of time.

The room temperature of each room after the completion of decontamination operations was about 30 to 32° C., and the relative humidity at that time was about 50 to 60%. In order to remove the hydrogen peroxide gas from each room targeted to be decontaminated, after discharge of the hydrogen peroxide gas had been stopped, airing in room was carried out and thereafter all the BI was re-collected.

TABLE 2

| TARGET ROOM NO. | CAPACITY ($m^3$) | DECONTAMINATION UNIT NO. | CONVEYANCE DISTANCE (m) | | | | Ax/Bx | HUMIDITY CONTROL SETTING (%) | DECONTAMINATION EFFECT |
| | | | MIST LINE (AX) | $H_2O_2$ LINE (BX) | AIR LINE | WATER LINE | | | |
|---|---|---|---|---|---|---|---|---|---|
| 1 | 29 | 1 | 6 | 2 | 1 | 2 | 3 | 40 | $10^{-6}$ |
| 2 | 14 | 2 | 8 | 2 | 1 | 2 | 4 | | $10^{-6}$ |
| 3 | 313 | 3 | 28 | 2 | 1 | 2 | 14 | | $10^{-6}$ |
| | | 4 | 25 | 2 | 1 | 2 | 12.5 | | |
| | | 5 | 27 | 2 | 1 | 2 | 13.5 | | |
| | | 6 | 37 | 2 | 1 | 2 | 18.5 | | |
| | | 7 | 27 | 2 | 1 | 2 | 13.5 | | |
| | | 8 | 24 | 2 | 1 | 2 | 12 | | |
| 4 | 22 | 9 | 20 | 2 | 1 | 2 | 10 | | $10^{-6}$ |
| 5 | 15 | 10 | 24 | 2 | 1 | 2 | 12 | | $10^{-6}$ | a case where the conveyance distance of the mixture mist pipes is long, advanced decontamination validation is possible.

Example 2

Example 2 was carried out based on the second embodiment. Incidentally, in the Example 2, rooms targeted to be decontaminated, of which capacities were different from those of the second embodiment described with reference to FIG. 2, were decontaminated. The rooms targeted to be decontaminated in Example 2 are five large and small clean rooms in medical and pharmaceutical manufacturing line, and the capacity of each room is shown in Table 2. In The re-collected BI was cultured by a predetermine method and then the degree of sterilization was determined. In the Example 2, the used BI is for 6-algorithm reduction, and determination was made assuming that 6-algorithm reduction was achieved as the condition that the sterilization indicator bacteria of all the re-collected BI were lethal. In the field of decontamination effect in Table 2, achievement of 6-algorithm reduction was represented as "$10^{-6}$". As is obvious from Table 2, in all of the rooms targeted to be decontaminated, 6-algorithm reduction was achieved, and in a case where the conveyance distance of the mixture mist pipes is long, advanced decontamination validation becomes possible.

As described above, as is obvious from each of the examples, in the present invention, there can be provided a decontamination system which does not require large scale equipment such as large diameter ducts is large or an anti-condensation heater, while enabling, with respect to a plurality of rooms targeted to be decontaminated, pipelining of which distance is long for each room, the decontamination system being capable of supplying an accurate amount of decontamination gas for each room.

Incidentally, when the present invention is carried out, the following modification examples are shown without being limited to each of the embodiments.

(1) Although in the embodiments, four or five rooms targeted to be decontaminated were decontaminated, without being limited thereto, and it may be that only one room is targeted to be decontaminated by the decontamination system, or alternatively, 10 or more rooms are targeted to be decontaminated.

(2) Although in the Example 1, humidity-control before decontamination was not carried out in particular, it may be that decontamination is carried out after humidity-control by a humidity controller provided in each room has been carried out.

(3) Although in the embodiments, an air compressor was employed as compressed air-generating means, without being limited thereto, other means such as a high-pressure pneumatic cylinder may be employed.

(4) Although in the embodiments, ejectors were employed as as-solution mixers, without being limited thereto, other gas-liquid mixing means such as a gas-liquid pump may be employed.

(5) Although in the embodiments, a distilled water tank was employed as water supplying means, without being limited thereto, other means such as a water supplying pipe may be employed.

(6) Although in the embodiments, tube pumps were employed in a pipeline of hydrogen peroxide water pipes and a pipeline of distilled water pipes, without being limited thereto, any other pump or solution-supplying means may be employed.

(7) Although in the embodiments, evaporators having an evaporation plate as gas generators were employed, without being limited thereto, other gas generators may be employed as long as it is possible to gasify mixture mist.

(8) Although in the embodiments, a circulating fan was employed in each room targeted to be decontaminated, without being limited thereto, for example, in a case where a room targeted to be decontaminated has its own air flow mechanism such as the RABS (Restricted Access Barrier System) or the LF (Laminar Flow), circulation of hydrogen peroxide gas in room may be carried out by these mechanisms. In addition, circulation of hydrogen peroxide gas may be carried out by an air conditioner apparatus or the like that has already been installed in a room targeted to be decontaminated.

DESCRIPTION OF REFERENCE NUMERALS

10 . . . Pneumatic compressor
11 to 15 . . . Air pipes
20 . . . Hydrogen peroxide water tank
21 to 25 . . . Hydrogen peroxide water pipes
31 to 35 . . . Ejectors
41 to 45 . . . Evaporators
51 to 55 . . . Circulating fans
61 to 65 . . . Mixture mist pipes
70 . . . Distilled water tank
71 to 75 . . . Distilled water pipes
100, 200 . . . Decontamination system
R1 to R4 . . . Rooms targeted to be decontaminated

The invention claimed is:

1. A decontamination system for decontaminating, with respect to one or more rooms targeted to be decontaminated, an inside of each room targeted to be decontaminated, by using decontamination gas, the decontamination system comprising compressed air-generating means for generating compression air; decontamination solution-supplying means for supplying decontamination solution;

mixed gas-liquid adjusters to adjust, with respect to each room targeted to be decontaminated, decontamination mixed gas-liquid obtained by respectively mixing the compression air and the decontamination solution;

gas generators to gasify the mixed gas-liquid to generate decontamination gas;

air supplying pipes which communicate from the compressed air-generating means up to each of the mixed gas-liquid adjuster;

decontamination solution supplying pipes which communicate from the decontamination solution-supplying means up to each of the mixed gas-liquid adjuster; and mixed gas-liquid supplying pipes which communicate from each mixed gas-liquid adjuster up to a corresponding gas generator of the gas generators, characterized in that the compressed air-generating means, the decontamination solution-supplying means, and each respective mixed gas-liquid adjusters are arranged at positions which are spaced from each room targeted to be decontaminated, and each of the gas generators is arranged near or in each of the one or more rooms targeted to be decontaminated that corresponds thereto, and a conveyance distance of each mixed gas-liquid supplying pipe with respect to each room targeted to be decontaminated is thereby longer than a conveyance distance of each of the decontamination solution supplying pipes that corresponds thereto.

2. The decontamination system according to claim 1, characterized in that, for at least one or all of the one or more rooms targeted to be decontaminated, the following formula is met:

$$Ax/Bx \geq 3 \quad (1)$$

where Ax is a conveyance distance of the mixed gas-liquid supplying pipes to the one or more rooms targeted to be decontaminated; where Bx is a conveyance distance of each of the corresponding decontamination solution supplying pipes to the one or more rooms targeted to be decontaminated; and where x is an integer of 1 to n, and corresponds to each room targeted to be decontaminated of n rooms targeted to be decontaminated.

3. The decontamination system according to claim 2, characterized in that compression air to be supplied from the compressed air-generating means to each mixed gas-liquid adjuster via each air supplying pipe is 0.05 MPa or more in ejection pressure and 5 NL/min to 70 NL/min in air flow rate, respectively, with respect to each mixed gas-liquid adjuster, and a decontamination solution to be supplied from the decontamination solution-supplying means to each mixed gas-liquid adjuster via each decontamination solution supplying pipe is 0.3 mL/min to 30 mL/min in flow rate, respectively, with respect to each mixed gas-liquid adjuster.

4. The decontamination system according to any one of claims 1 to 3, having water supplying means for supplying water for controlling humidity in the one or more rooms targeted to be decontaminated, the decontamination system comprising water supplying pipes which respectively communicate from the water supplying means up to the mixed gas-liquid adjuster associated with each room targeted to be decontaminated, characterized in that, with respect to the mixed gas-liquid adjusters, supply of water via the water supplying pipes and supply of the decontamination solution via the decontamination solution supplying pipes are coupled to each other with a respective mixed gas-liquid adjuster, when water is supplied to the mixed gas-liquid adjuster, a humidification mixed gas-liquid obtained by mixing the compression air and water is adjusted by the mixed gas-liquid adjusters, and the humidification mixed gas-liquid is supplied to the gas generators via the mixed gas-liquid supplying pipes and then the humidification mixed gas-liquid is gasified to generate humidification gas of water vapor, and when the decontamination solution is supplied to each mixed gas-liquid adjuster, a decontamination mixed gas-liquid obtained by mixing the compression air and the decontamination solution is adjusted by the mixed gas-liquid adjusters, and the decontamination mixed gas-liquid is supplied to each gas generator via the mixed gas-liquid supplying pipes and then the decontamination mixed gas-liquid is gasified to generate decontamination gas.

5. A decontamination method, characterized by using the decontamination system according to any one of claims 1 to 3 and comprising, supplying the decontamination solution to the mixed gas-liquid adjusters to thereby decontaminate an inside of each room targeted to be decontaminated by decontamination gas.

6. A decontamination method, characterized by using the decontamination system according to claim 4 and comprising, first, supplying water to the mixed gas-liquid adjusters to obtain a humidification mixed gas-liquid that is gasified by the gas generators to thereby control a humidity to a preset value in each room targeted to be decontaminated, and next, supplying the decontamination solution to each mixed gas-liquid adjuster to thereby decontaminate an inside of each room targeted to be decontaminated by decontamination gas.

* * * * *

UNITED STATES PATENT AND TRADEMARK OFFICE
CERTIFICATE OF CORRECTION

PATENT NO. : 10,426,856 B2
APPLICATION NO. : 15/300729
DATED : October 1, 2019
INVENTOR(S) : Kawasaki et al.

It is certified that error appears in the above-identified patent and that said Letters Patent is hereby corrected as shown below:

In the Claims

Column 20, Claim 1, Line 20, "adjuster" should be -- adjusters --.

Column 20, Claim 1, Line 23, "adjust" should be -- adjusters --.

Signed and Sealed this
Nineteenth Day of November, 2019

Andrei Iancu
*Director of the United States Patent and Trademark Office*